United States Patent
Mahalingam et al.

(10) Patent No.: US 8,808,765 B2
(45) Date of Patent: Aug. 19, 2014

(54) COSMETIC COMPOSITIONS AND METHODS FOR USING SAME TO IMPROVE THE AESTHETIC APPEARANCE OF SKIN

(75) Inventors: Harish Mahalingam, Ledgewood, NJ (US); Christos D. Kyrou, Goshen, NY (US); Michael Traudt, Brookfield, CT (US); Dmitri S. Ptchelintsev, Jersey City, NJ (US)

(73) Assignee: Avon Products, Inc, New York, NY (US)

( * ) Notice: Subject to any disclaimer, the term of this patent is extended or adjusted under 35 U.S.C. 154(b) by 44 days.

(21) Appl. No.: 13/584,136

(22) Filed: Aug. 13, 2012

(65) Prior Publication Data

US 2012/0315344 A1 Dec. 13, 2012

Related U.S. Application Data

(63) Continuation of application No. 10/436,310, filed on May 12, 2003, now abandoned.

(51) Int. Cl.
*A61K 8/46* (2006.01)

(52) U.S. Cl.
USPC .......................................... 424/747; 514/550

(58) Field of Classification Search
CPC ......................................................... A61K 8/37
USPC .......................................... 424/747; 514/550
See application file for complete search history.

(56) References Cited

U.S. PATENT DOCUMENTS

| | | | |
|---|---|---|---|
| 7,241,456 B2 * | 7/2007 | Vromen | 424/449 |
| 2003/0068349 A1 * | 4/2003 | Jentzsch et al. | 424/401 |

* cited by examiner

*Primary Examiner* — Jake Vu
(74) *Attorney, Agent, or Firm* — David M. Joyal; Joan M. McGillycuddy

(57) ABSTRACT

The present invention relates to compositions useful in treating the various signs of dermatological aging in human skin. The present invention also relates to cosmetic compositions and methods of using such compositions that improve the aesthetic appearance of skin. Further, the present invention relates to methods of applying the compositions to the skin to effect treatment and to improve the aesthetic appearance of skin, particularly, by providing anti-aging benefits to the skin. Suitable anti-aging agents include 3,3'-thiodipropionic acid and/or its derivatives.

6 Claims, No Drawings

COSMETIC COMPOSITIONS AND METHODS FOR USING SAME TO IMPROVE THE AESTHETIC APPEARANCE OF SKIN

RELATED APPLICATIONS

This is a continuation application that claims priority to, and the benefit of, U.S. Ser. No. 10/436,310, filed May 12, 2003 now abandoned, which is a continuation-in-part application that claims priority to, and the benefit of U.S. Ser. No. 09/741,383, filed Dec. 20, 2000, the contents of which application are hereby incorporated by reference in their entirety.

BACKGROUND OF THE INVENTION

1. Field of the Invention

The present invention relates to compositions useful in treating hyperpigmentation and the various signs of dermatological aging in human skin. The present invention also relates to cosmetic compositions and methods of using such compositions that improve the aesthetic appearance of skin. Further, the present invention relates to methods of applying the compositions to the skin to effect treatment and to improve the aesthetic appearance of skin, particularly, by providing anti-aging benefits to the skin.

2. Description of the Prior Art

Human skin color is determined primarily by the content of the pigment melanin in the basal epidermis layer. Melanin is synthesized by the process of melanogenesis within melanocytes (pigment-producing cells). Melanin is deposited onto melanosomes, which are transferred to keratinocytes in the basal epidermal layer. Melanosomes present in these basal keratinocytes are the key determinants of skin color. The keratinocytes leave the basal layer and undergo differentiation forming the cornified top layer of the skin. Once the keratinocytes leave the basal layer, the melanosomes lose their characteristic electron dense structure, and the load of melanin is carried to the surface of the skin by the differentiating keratinocytes.

The skin can become hyperpigmented when too much melanin concentrates at one area or portion of the skin due to the retention time of the melanosomes in the basal layer. Hyperpigmentation can also occur as a result of overexposure to the sun or other inflammatory stimuli. Hyperpigmentation can take the form of solar lentigines (age spots), ephilides (freckles), melasma, chloasma, and pigmented keratoses.

The prior art discloses ways to treat hyperpigmentation by application of skin lightening agents. Representative skin lightening agents include hydroquinone and Vitamin C. Such agents typically lighten the skin by inhibiting the expression of tyrosinase enzymes involved in melanogenesis.

It would be desirable to have a way to treat hyperpigmentation by application of agents that reduce the ability of epidermal cells to retain melanin. A reduction in ability to retain melanin would speed the transfer of the melasonomes to the keratinocytes and allow existing hyperpigmented portions of the skin to be lightened or de-pigmented faster than with conventional skin lightening agents, which act primarily to inhibit the formation of new melanin.

There is active contemporary interest in the cosmetics industry to develop products that may be applied topically to the skin that provide anti-aging, hydrating, and/or skin texturizing benefits. Cosmetic products, which enhance the appearance of skin, are increasingly in demand. Consumers are interested in mitigating or delaying the signs of aged or photo-aged skin, such as fine lines, wrinkles, drying, and sagging skin. During the aging process, the complexion of the skin, i.e., the color and appearance of the skin, deteriorates slowly from aging and/or exposure to sunlight. Cosmetic surgery can be used as a treatment for aged skin. However, such treatment is costly and carries the risks normally associated with anesthesia and surgery. Alternatively, cosmetic products that provide anti-aging benefits are highly desirable, to both manufacturers and consumers.

The number of cosmetic products directed to help the skin of consumers look younger and less wrinkled is steadily increasing. Commonly, such products contain exfoliating acids as active ingredients. Such anti-aging active ingredients include, for example, a-hydroxy acids (e.g., lactic, glycolic, citric), b-hydroxy acids (e.g., salicylic; 5-n-octanoylsalicylic acids) and retinoids (retinoic acids; retinol). It is known that these anti-aging active ingredients have a significant disadvantage in that they frequently are associated with consumer discomfort characterized by burning, smarting, itching or sensation of tightness after application. There remains a general need in the cosmetics industry for products that retard or counter aging effects on the skin, and more specifically for products that produce such effects without undesirable side effects.

Also, in spite of the various anti-aging cosmetic products on the market for the treatment of skin, there remains a need for effective anti-aging compositions that can be applied topically to the skin. More particularly, there remains a need for topically applied cosmetic compositions that have anti-aging and skin texture benefits.

SUMMARY OF THE INVENTION

It is an object of the present invention to provide a composition and method for treating, preventing and/or ameliorating hyperpigmentation of human skin.

It is a further object of the present invention to provide a composition and method for treating, preventing and/or ameliorating the signs of dermatological aging of human skin.

It is yet a further object of the present invention to provide cosmetic compositions and methods of using such cosmetic compositions that improve the aesthetic appearance of skin and remediate the effects of aging skin and signs of aging on skin.

It is still another object of the present invention to provide such a composition and method that has one or more agents that decrease the retention time of melanosomes at the basal layer. This is achieved by inhibiting the ability of epidermal cells to retain or uptake melanin/melanosomes and/or increase the rate of transport of basal keratinocytes to the surface of the skin.

These and other objects of the present invention are achieved by a method and composition that comprises (a) a de-pigmenting agent or anti-aging agent in an amount effective to prevent, treat and/or ameliorate pigmentation or the various signs of aging at an area of skin to which it is applied, and (b) a cosmetically or pharmaceutically acceptable vehicle. Suitable de-pigmenting agents include 3,3'-thiodipropionic acid, thiazolidine-2-carboxylic acid, Kaempferol-7-glucoside, perilla oil, and clofibrate and clofibrate analogs and/or derivatives, as well as those set forth below. Suitable anti-aging agents include 3,3'-thiodipropionic acid and/or its derivatives.

DETAILED DESCRIPTION OF THE INVENTION

The present invention provides for de-pigmenting compositions containing an effective amount of one or more depigmenting agents which, when applied to human skin, prevent, treat and/or ameliorate pigmentation at the area or portion of skin to which they are applied. The compositions are effective at reducing or diminishing pigmented areas or portions of the skin such as age spots, freckles, melasma, chloasma, and pigmented keratoses. The compositions are topically applied to the skin.

The present invention also provides for anti-aging compositions containing an effective amount of one or more ingredients which, when applied to human skin, prevent, treat and/or ameliorate the various signs of aging at the area or portion of skin to which they are applied. The present invention provides anti-aging benefits to and improves the aesthetic appearance of the skin. In particular, the present invention provides compositions and methods for treating skin to prevent, inhibit, reduce and/or ameliorate the signs of dermatological aging due to, for example, chronological aging, hormonal aging, and/or photoaging. Such signs of aging include, but are not limited to skin fragility; loss of collagen and/or elastin; estrogen imbalance in skin; skin atrophy; appearance and/or depth of lines and/or wrinkles, including fine lines; skin discoloration, including dark eye circles; skin sagging; skin fatigue and/or stress, e.g. skin breakout due to environmental stress, such as pollution and/or temperature changes; skin dryness; skin flakiness; cellular aging; loss of skin tone, elasticity and/or luster; loss of skin firmness; poor skin texture; loss of skin elasticity and/or resiliency; and thin skin.

The benefits and improvements to the aesthetic appearance of skin can be manifested in any of the following: reduction in pore size; improvement in skin tone, radiance, clarity and/or tautness; promotion of anti-oxidant activity; improvement in skin firmness, plumpness, suppleness, and/or softness; improvement in procollagen and/or collagen production; improvement in skin texture and/or promotion of retexturization; improvement in skin barrier repair and/or function; improvement in appearance of skin contours; restoration of skin luster and/or brightness; replenishment of essential nutrients and/or constituents in the skin decreased by aging and/or menopause; improvement in communication among skin cells; increase in cell proliferation and/or multiplication; increase in skin cell metabolism decreased by aging and/or menopause; improvement in skin moisturization; promotion and/or acceleration of cell turnover; enhancement of skin thickness; increase in skin elasticity and/or resiliency; and enhancement of exfoliation, with or without the use of alpha or beta hydroxy acids, keto acids or other exfoliants.

A first embodiment of the present composition has a compound corresponding to the following Formula (I):

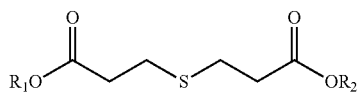

(I)

wherein $R_1$ and $R_2$ are independently selected from the group of substituents consisting of hydrogen; alkyls, substituted or unsubstituted, branched or linear; alkenyls, substituted or unsubstituted, branched or linear, and having up to 5 double bonds; alkynyls, substituted or unsubstituted, branched or linear and having up to 5 triple bonds; aryls, substituted or unsubstituted; cycloalkyls, substituted and unsubstituted; and cycloalkenyls, substituted and unsubstituted. Formula I compounds shall be referred to herein as either "de-pigmenting agents" or "anti-aging agents".

Preferably, the Formula I compound is 3,3'-thiodipropionic acid, wherein $R_1$ and $R_2$ are hydrogen.

A second embodiment of the present composition has a de-pigmenting agent corresponding to formula II:

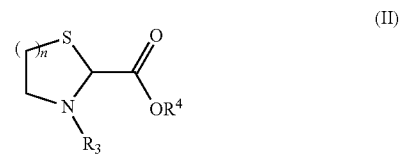

(II)

wherein $R_3$ and $R_4$ are defined the same as $R_1$ and $R_2$ in formula (I) above; in addition, $R_3$ can be an acyl group; wherein "n" is an integer from 1 to 4, preferably 1 to 3, and most preferably 1 to 2.

Preferably, the de-pigmenting composition of Formula II is thiazolidine-2-carboxylic acid, wherein $R_3$ and $R_4$ are hydrogen and n=1.

In a third embodiment of the present composition, the de-pigmenting agent is perilla oil. Perilla oil is derived from the seeds of the mint of the genus *Perilla*.

In a fourth embodiment of the present composition, the de-pigmenting agent is clofibrate or a clofibrate analog or derivative. Clofibrate is ethyl 2-(p-chlorophenoxy)isobutyrate, which corresponds to the following formula (IV):

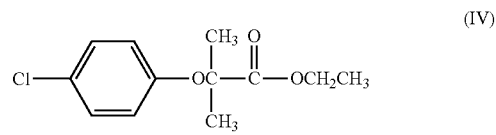

(IV)

A fifth embodiment of the present composition has a de-pigmenting agent corresponding to the following formula (III):

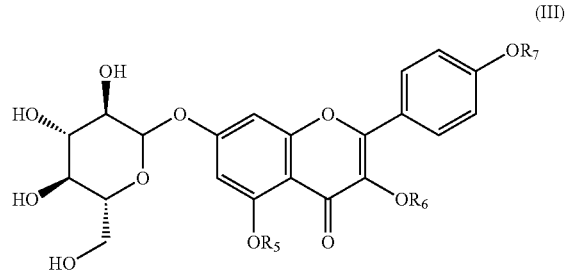

(III)

wherein $R_5$, $R_6$, and $R_7$ are as defined as for $R_1$ and $R_2$ in formula (I) above.

Preferably, the de-pigmenting agent of Formula III is kaempferol-7-glycoside wherein $R_5$, $R_6$ and $R_7$ are hydrogen. Kaempferol-7-glycoside is believed to reduce pigmentation by inhibiting tyrosinase but may also reduce pigmentation by alternate pathways.

In a sixth embodiment of the present invention, the de-pigmenting agent is a combination of one or more of the above de-pigmenting agents. Preferably, the combination includes de-pigmenting agents that utilize different mechanisms of action. A preferred combination includes kaempferol-7-glucoside and perilla oil or clofibrate (or a clofibrate analog or derivative).

The de-pigmenting agent is present in the composition at an amount effect to prevent, treat, or ameliorate pigmentation at the area or portion of skin to which it is applied. The de-pigmenting agent is preferably present at about 0.0001 percentage by weight (wt %) to about 98 wt %, more preferably at about 0.001 wt % to about 30 wt %, and most preferably at about 0.05 wt % to about 10 wt % based on the total weight of the composition. The composition is preferably applied to an affective area of skin for a period of time prevent, treat, or ameliorate pigmentation of the area of skin to which the composition is applied. As can be understood by those in the art, the amount of times per day and the period of time that the composition is to be applied to be effective will vary according to the percentage of active used in the composition, the additional ingredients in the composition (e.g., whether or not there is a penetration enhancer or additional depigmenting agents), as well as other factors known by those skilled in the art.

The anti-aging agent is present in the composition at an amount effect to prevent, treat, or ameliorate the various signs of aging in the area or portion of skin to which it is applied. The anti-aging agent is preferably present at about 0.0001 percentage by weight (wt %) to about 98 wt %, more preferably at about 0.001 wt % to about 30 wt %, and most preferably at about 0.05 wt % to about 10 wt % based on the total weight of the composition. The composition is preferably applied to an affective area of skin for a period of time to improve the aesthetic appearance of the area of skin to which the composition is applied. As can be understood by those in the art, the amount of times per day and the period of time that the composition is to be applied to be effective will vary according to the percentage of active used in the composition, the additional ingredients in the composition (e.g., whether or not there is a penetration enhancer or additional anti-agents), the targeted improvement as well as other factors known by those skilled in the art.

In particular, the present invention provides compositions and methods for treating skin to prevent, inhibit, reduce and/or ameliorate the signs of dermatological aging due to, for example, chronological aging, hormonal aging, and/or photoaging. Such signs of aging include, but are not limited to skin fragility; loss of collagen and/or elastin; estrogen imbalance in skin; skin atrophy; appearance and/or depth of lines and/or wrinkles, including fine lines; skin discoloration, including dark eye circles; skin sagging; skin fatigue and/or stress, e.g. skin breakout due to environmental stress, such as pollution and/or temperature changes; skin dryness; skin flakiness; cellular aging; loss of skin tone, elasticity and/or luster; loss of skin firmness; poor skin texture; loss of skin elasticity and/or resiliency; and thin skin.

The benefits and improvements to the aesthetic appearance of skin can be manifested in any of the following: reduction in pore size; improvement in skin tone, radiance, clarity and/or tautness; promotion of anti-oxidant activity; improvement in skin firmness, plumpness, suppleness, and/or softness; improvement in procollagen and/or collagen production; improvement in skin texture and/or promotion of retexturization; improvement in skin barrier repair and/or function; improvement in appearance of skin contours; restoration of skin luster and/or brightness; replenishment of essential nutrients and/or constituents in the skin decreased by aging and/or menopause; improvement in communication among skin cells; increase in cell proliferation and/or multiplication; increase in skin cell metabolism decreased by aging and/or menopause; improvement in skin moisturization; promotion and/or acceleration of cell turnover; enhancement of skin thickness; increase in skin elasticity and/or resiliency; and enhancement of exfoliation, with or without the use of alpha or beta hydroxy acids, keto acids or other exfoliants.

When a composition according to the present invention includes a Formula I compound, the compositions on are preferably used in methods of improving, ameliorating or treating the following signs of aging skin: texture, clarity, pigmentation (mottled and/or discrete), fine wrinkles, coarse wrinkles, sallowness, laxness, sagging, turgor, undereye puffiness, and/or overall photodamage. Preferably, the Formula I compound is 3,3'-thiodipropionic acid and/or a derivative thereof. Most preferably, the Formula I compound is 3,3'-thiodipropionic acid.

The compositions of the present invention comprise a pharmaceutically and/or cosmetically acceptable vehicle to provide bulk and physical form. Preferably, the vehicle is hypoallergenic, as allergens and other irritating agents exacerbate pigmentation. Suitable vehicles include, but are not limited to, cetyl alcohol, ethanol, glycerin, myristyl palmitate, polyvinyl alcohol, propylene glycol, propanol, and water, and mixtures thereof. The depigmenting/anti-aging agent is admixed with the vehicle(s) along with any other adjuvants or ingredients to form the topical composition. The compositions of the present invention may also include actives in the form of liposomes.

The present composition may take any suitable form such as a solution, cream, serum, stick, patch, mask, towelette, lotion, emulsion, ointment or gel.

The present composition may optionally have one or more of the following ingredients: anesthetics, antiallergenics, antimicrobial agents, antiseptics, chelating agents, colorants, demulcents, emollients, emulsifiers, exfolients, fragrances, humectants, lubricants, moisturizers, preservatives, skin penetration enhancers, stabilizers, surfactants, thickeners, viscosity modifiers, vitamins, and mixtures thereof.

The present invention may also include conventional cosmetic acitive agents, such as other conventional hypopigmenting agents, such as hydroquinone, ascorbic acid (Vitamin C) and/or licorice extract; retinoids, such as retinol or retinoic acid; anti-inflammatory agents, such as bisabolol, anti-acne agents, such as salicylic acid; exfoliants, such as alpha-hydroxy acids, beta-hydroxy acids, keto acids, oxa acids or oxa diacids (disclosed in U.S. Pat. Nos. 5,847,003 and 5,834,513); ascorbyl-phosphoryl-cholesterol (disclosed in U.S. Pat. No. 5,866,147); sunscreens, such as oxybenzone, octyl methoxycinnamate, octyl salicylate, octocrylene, titanium dioxide, zinc oxide, butyl methoxydibenzoylmethane, methylene bis-benzotriazoylteramehtylbuthylphenol (MBBT), bis-ethylhexyl oxyphenol methoxyphenol triazine (BEMT); or anti-aging agents; or any combination thereof. When conventional hypopigmenting agents are included in a composition of the present invention, it is preferred that the hypopigmenting agent has a mechanism of action that complements the mechanism of action of the depigmenting agent of the present invention. Preferred alpha-hydroxy acids include lactic acid, glycolic acid, or a mixture thereof. The preferred oxa diacid is 3,6,9-trioxaundecanedioic acid.

Formula I compounds, preferably 3,3'-thiodipropionic acid, may be used to enhance the effectiveness of other skin care actives, such as those disclosed above and those skin care actives disclosed in U.S. Pat. No. 6,492,326 at col. 5, lines 9 through col. 20, line 50, which is incorporated herein by reference.

EXAMPLE

| Ingredient | wt % |
|---|---|
| De-pigmenting agent or anti-aging agent e.g. (3,3'-thiodipropionic acid) | 0.001 to 98 |
| pH adjusting agent (e.g. ammonium | 0.001 to 4 |
| Humectants (e.g. glycols, glycerols) | 0.5 to 15 |
| Thickeners (e.g. gums, starches polymers) | 0.1 to 4 |
| Chelating Agents (e.g. EDTA) | 0.001 to 0.5 |
| Emollients (e.g. isopropyl myristate, fatty esters) | 1 to 10 |
| Silicones (cyclomethicone-pentamer) | 0.1 to 15 |
| Preservative (e.g. parabens) | 0.01 to 2 |
| Alcohols (e.g. ethanol) | 0 to 10 |
| Antioxidants (e.g. vitamin E acetate) | 0.01 to 5 |
| Anti-inflammatory (e.g. bisabolol) | 0.01 to 10 |
| Sunscreen (e.g. titanium dioxide/benzophenone-3, Butyl methoxydibenzoylmethane) | 0.01 to 15 |
| Water | q.s. |

When the compositions of the present invention are used to improve the aesthetic appearance of skin or to improve, ameliorate and/or treat the signs of aging skin, the preferred anti-aging agent is 3,3'-thiodipropionic acid. It is more preferred that in addition to 3,3'-thiodipropionic acid, the cosmetic composition includes at least one ingredient selected from the group consisting of: palmatoyl tetrapeptide-3 (available under the trade name RIGIN from Sederma, France), *Gynostemma pentaphyllum* and/or an extract therefrom, *Stenoloma chusana* and/or an extract therefrom, *Morinda citrifolia* and/or an extract therefrom, *Butea frondosa* and/or an extract therefrom, Luteoline 7-beta-glucoside, Chlorosalicylic Acid, *Naringi crenulata* and/or an extract therefrom, Methylthioadenosine, Ferutinin, *Ilex purpurea* and/or an extract therefrom, *Asmunda japonica* and/or an extract therefrom, Rhapontin, *Uncaria gambir* and/or an extract therefrom, Iopanic acid, Ellagic acid, 2,4,6,3,4-pentahydroxychalcone, *Ligusticum chianxiong* or an extract therefrom, *Azadirachta indica* (Neem) and/or an extract therefrom, *Aframomum melegueta* and/or an extract therefrom, 2-amino-4,5-methyl thiazole, or any combination thereof. More preferably, the cosmetic composition contains at least two ingredients selected from the foregoing group.

The present invention having been described with particular reference to the preferred forms thereof, it will be obvious that various changes and modifications may be made herein without departing from the spirit and scope of the invention as defined in the appended claims. As used herein, singular can mean plural.

What is claimed is:

1. A method for improving the aesthetic appearance of skin comprising topically applying to wrinkled skin a cosmetic composition comprising (i) from about 0.0001 to about 30% by weight of the total composition of a compound according to Formula (I):

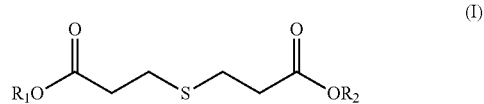

and (ii) a cosmetically acceptable vehicle in the form of an emulsion comprising water and an emulsifier, wherein $R_1$ and $R_2$ are independently selected from the group of substituents consisting of hydrogen; alkyls, substituted or unsubstituted, branched or linear; alkenyls, substituted or unsubstituted, branched or linear, and having up to 5 double bonds; alkynyls, substituted or unsubstituted, branched or linear and having up to 5 triple bonds; aryls, substituted or unsubstituted; cycloalkyls, substituted and unsubstituted; and cycloalkenyls, substituted and unsubstituted, and wherein the compound according to Formula I is present in said cosmetic composition in an amount effective to reverse the loss of collagen and/or elastin and to reduce the appearance and/or depth of wrinkles on the wrinkled skin; and with the proviso that said composition does not comprise methylthioadenosine.

2. The method of claim 1, wherein the compound of Formula (I) is 3,3'-thiodipropionic acid.

3. The method of claim 1, wherein the compound of Formula (I) is present in an amount of from about 0.001 to about 10% by weight of the composition.

4. The method of claim 3, further comprising an ingredient selected from the group consisting of retinoid, salicylic acid, an oxa acid, oxa diacid, an alpha hydroxy acid, a beta hydroxy acid, and any combination thereof.

5. The method of claim 2, wherein 3,3'-thiodipropionic acid is present in the composition in an amount of from about 0.001 to about 10% by weight of the composition.

6. The method of claim 4, further comprising an ingredient selected from the group consisting of lactic acid, glycolic acid, 3,6,9-trioxaundecanoic acid, and any combination thereof.

* * * * *